United States Patent
Digasbarro

(10) Patent No.: US 11,642,509 B2
(45) Date of Patent: May 9, 2023

(54) HUB CLEANING DEVICE FOR MEDICAL CONNECTORS AND METHOD OF USE

(71) Applicant: Trademark Medical L.L.C., Ballwin, MO (US)

(72) Inventor: Phillip Peter Digasbarro, St. Louis, MO (US)

(73) Assignee: TRADEMARK MEDICAL L.L.C., Ballwin, MO (US)

( * ) Notice: Subject to any disclaimer, the term of this patent is extended or adjusted under 35 U.S.C. 154(b) by 0 days.

(21) Appl. No.: 17/551,880

(22) Filed: Dec. 15, 2021

(65) Prior Publication Data

US 2022/0193388 A1 Jun. 23, 2022

Related U.S. Application Data

(60) Provisional application No. 63/126,804, filed on Dec. 17, 2020.

(51) Int. Cl.
| | | |
|---|---|---|
| *A61M 39/16* | (2006.01) | |
| *B08B 9/02* | (2006.01) | |
| *B08B 9/027* | (2006.01) | |
| *A61M 39/10* | (2006.01) | |

(52) U.S. Cl.
CPC ............ *A61M 39/16* (2013.01); *B08B 9/021* (2013.01); *B08B 9/027* (2013.01); *A61M 2039/1033* (2013.01); *A61M 2209/10* (2013.01)

(58) Field of Classification Search
CPC .......... A61M 39/16; A61M 2039/1033; A61M 2209/10; B08B 9/021; B08B 9/027
See application file for complete search history.

(56) References Cited

U.S. PATENT DOCUMENTS

| | | |
|---|---|---|
| 1,766,341 A | 6/1930 | Irving |
| 4,233,025 A | 11/1980 | Larson et al. |
| 4,551,146 A * | 11/1985 | Rogers ................ A61M 39/165 285/376 |
| 5,066,527 A | 11/1991 | Newell |

(Continued)

OTHER PUBLICATIONS

Quellen. *Cleaning ENFit in the Neonatal Intensive Care Unit.* May 2018. https://www.medela.us/breastfeeding-professionals/blog/cleaning-enfit-in-the-neonatal-intensive-care-unit.

(Continued)

*Primary Examiner* — Sharidan Carrillo
(74) *Attorney, Agent, or Firm* — Diederiks & Whitelaw, PLC.

(57) ABSTRACT

A cleaning device is configured access and remove fluid from and dry a moat region defined by a hub of a medical connector, thereby minimizing the potential for bacterial growth in the hub. The cleaning device takes the form of an absorbent block which can be inserted into the moat by extending about a central male fitting and into a gap between the male fitting and the inner wall of a female hub of the medical connector. In a preferred embodiment of the invention, the block takes the form of a tubular cylinder particularly configured for use on ENFit medical connectors wherein the absorptive feature of the cleaning device can be employed alone or in combination with another cleaning tool used to first remove any existing dried and caked solution in the hub before removing residual cleaning fluid from the moat.

11 Claims, 18 Drawing Sheets

(56) References Cited

U.S. PATENT DOCUMENTS

| | | | |
|---|---|---|---|
| 6,810,552 B2 | 11/2004 | Miyake et al. | |
| 7,993,309 B2 | 8/2011 | Schweikert | |
| 8,252,247 B2 | 8/2012 | Ferlic | |
| 8,336,151 B2 | 12/2012 | Kerr et al. | |
| 8,696,820 B2 | 4/2014 | Vaillancourt | |
| 8,808,637 B2 | 8/2014 | Ferlic | |
| 9,129,449 B2 | 9/2015 | Davidson | |
| 9,186,707 B2 | 11/2015 | Vaillancourt et al. | |
| 9,259,284 B2 | 2/2016 | Rogers et al. | |
| 9,352,140 B2 | 5/2016 | Kerr et al. | |
| 9,572,904 B2 | 2/2017 | Ferlic | |
| 9,707,308 B2 | 7/2017 | Ferlic et al. | |
| 9,907,617 B2 | 3/2018 | Rogers | |
| 9,931,176 B2 | 4/2018 | Davis et al. | |
| 9,999,471 B2 | 6/2018 | Rogers et al. | |
| 10,166,085 B2 | 1/2019 | Ready et al. | |
| 10,188,842 B2 | 1/2019 | Moore | |
| 10,195,000 B2 | 2/2019 | Rogers et al. | |
| D842,565 S | 3/2019 | Davis et al. | |
| 10,220,419 B2 | 3/2019 | Ryan et al. | |
| 10,357,579 B2 | 7/2019 | Chiu et al. | |
| 10,449,575 B2 | 10/2019 | Ryan et al. | |
| 10,576,173 B2 | 3/2020 | Chiu et al. | |
| 10,576,261 B2 | 3/2020 | Chiu et al. | |
| 10,589,080 B2 | 3/2020 | Hitchcock et al. | |
| 10,675,121 B2 | 6/2020 | Davis et al. | |
| 2002/0166190 A1 | 11/2002 | Miyake et al. | |
| 2006/0030827 A1 | 2/2006 | Raulerson | |
| 2010/0000040 A1 | 1/2010 | Shaw et al. | |
| 2010/0003067 A1 | 1/2010 | Shaw et al. | |
| 2010/0083452 A1 | 4/2010 | Vaillancourt | |
| 2010/0192975 A1 | 8/2010 | Schweikert | |
| 2010/0200017 A1 | 8/2010 | Kerr et al. | |
| 2010/0242993 A1 | 9/2010 | Hoang et al. | |
| 2011/0265825 A1 | 11/2011 | Rogers et al. | |
| 2011/0314619 A1 | 12/2011 | Schweikert | |
| 2012/0315201 A1 | 12/2012 | Ferlic et al. | |
| 2013/0197485 A1 | 8/2013 | Gardner et al. | |
| 2014/0261558 A1 | 9/2014 | Rogers et al. | |
| 2014/0366914 A1 | 12/2014 | Kerr et al. | |
| 2016/0015931 A1 | 1/2016 | Ryan et al. | |
| 2016/0045629 A1 | 2/2016 | Gardner et al. | |
| 2016/0214142 A1 | 7/2016 | Davis et al. | |
| 2017/0042637 A1 | 2/2017 | Reinard et al. | |
| 2017/0143447 A1 | 5/2017 | Rogers et al. | |
| 2017/0157386 A1 | 6/2017 | Ferlic | |
| 2017/0165467 A1 | 6/2017 | Chiu et al. | |
| 2017/0232121 A1 | 8/2017 | Chiu et al. | |
| 2017/0333156 A1 | 11/2017 | Ready et al. | |
| 2018/0214242 A1 | 8/2018 | Davis et al. | |
| 2019/0076885 A1 | 3/2019 | Ryan et al. | |
| 2019/0099239 A1 | 4/2019 | Ready et al. | |
| 2019/0110861 A1 | 4/2019 | Davis et al. | |
| 2019/0117332 A1 | 4/2019 | Davis et al. | |
| 2019/0151643 A1 | 5/2019 | Alpert | |
| 2019/0192843 A1 | 6/2019 | Davis et al. | |
| 2019/0209826 A1 | 7/2019 | Breslin | |
| 2019/0282795 A1 | 9/2019 | Fangrow | |
| 2019/0290790 A1 | 9/2019 | Chiu et al. | |
| 2019/0351211 A1 | 11/2019 | Dombrowski et al. | |
| 2019/0351212 A1 | 11/2019 | Dudar et al. | |
| 2022/0193388 A1* | 6/2022 | Digasbarro | B08B 9/027 |

OTHER PUBLICATIONS

Quellen. *Cleaning ENFit in the NICU: What You Need to Know.* Oct. 2019. https://www.medela.us/breastfeeding-professionals/blog/cleaning-enfit-in-the-nicu-what-you-need-to-know.

ENFit Cleaning Procedures. *Feeding Tubes with Male ENFit Connectors.* GEDSA, 2018.

ENFit Cleaning Procedures. *Low Profile Feeding Tubes Extension Sets.* GEDSA, 2018.

EnClean Instructions for Use. EnClean, 2017. http://www.encleantube.com/using-the-brush.

NeoMed. *NeoConnect Cleaning Tool.* https://www.neomedinc.com/product/cleaning-tool-2/.

Centrix GingiTrac, Hands-Free Gingival Retraction System. 2016. https://www.centrixdental.com/gingicap.html.

Premier Inspired solutions for daily dentistry. *Traxodent Hemodent Paste Retraction System.* Premier Dental Products Company. 2017. Dental tooth caps (hollow caps for endodontic gum retraction around teeth).

\* cited by examiner

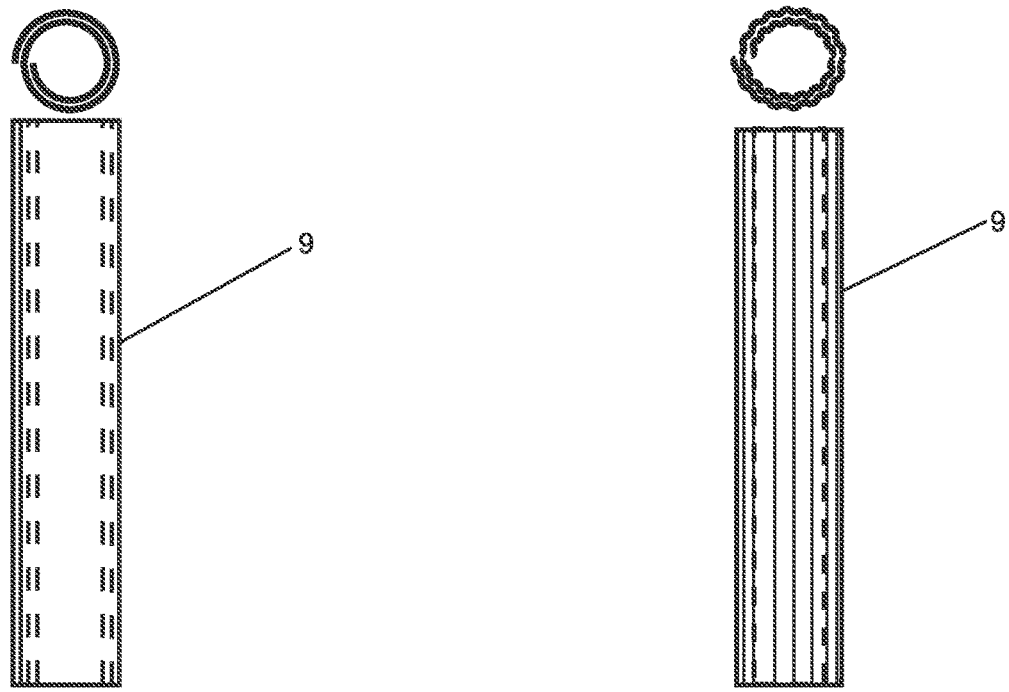
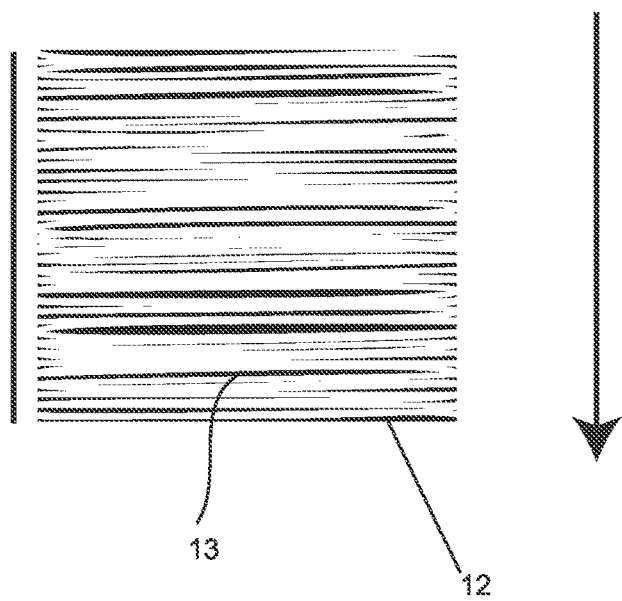
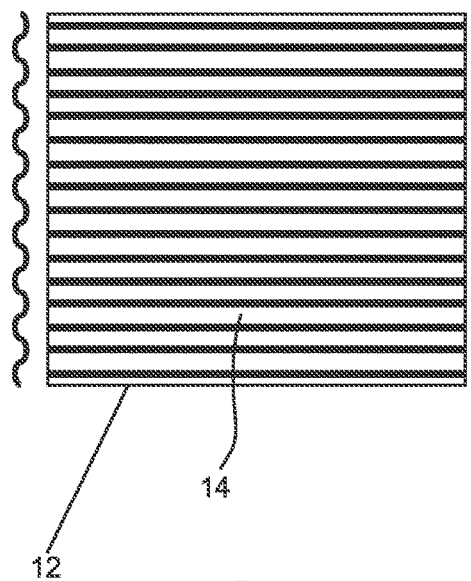
FIG. 5A  FIG. 5B

HUB CLEANING DEVICE FOR MEDICAL CONNECTORS AND METHOD OF USE

BACKGROUND OF THE INVENTION

Medical devices have long employed standardized universal connectors to insure leak proof connections between a wide range of devices. These connectors include luer taper connectors found in IV tubing and catheters, syringes and certain enteral feeding devices. However, this universal compatibility allows for accidental connections between devices that ought not to be connected, potentially resulting in patient injuries. A common example is the misconnection of an enteral feeding administration set with an intravenous line.

This problem has been recognized and, in the field of enteral feeding, has led to a new international standard being adopted for a set of unique connectors which do not allow an enteral feeding device to be connected to any other type of medical device connector, thus preventing misconnections. This new standard, developed by the Global Enteral Device Supplier Association (GEDSA), called ENFit, includes a standardized design for the male and female connectors of an enteral feeding system. While this system is expected to be successful in reducing misconnections, the geometry of the ENFit components has created some problems in clinical practice. One such problem is maintaining the cleanliness between the ENFit connector on the administration tubing set and the mating ENFit connector on the enteral feeding tube.

The enteral feeding tube is designed to remain in the patient for up to 30 days, but the administration tubing used to deliver the enteral feeding solution to the feeding tube from a bag, syringe or reservoir, may be changed multiple times per day. During each of these administration tubing changes there is an opportunity for enteral feeding solution to leak into, and remain in, the ENFit feeding tube connector where it can dry and cause caking. In time, drying and caking can result in difficulty connecting and disconnecting the administration tubing from the feeding tube. In fact, excessive caking may cause the connectors to stick together, leading to damage during disconnection and possibly requiring replacement of the feeding tube which is expensive and represents a risk to the patient.

With the above in mind, it is desirable to keep the ENFit feeding tube connector clean to prevent drying and caking of any enteral feeding solution that may remain in the connector after each treatment and administration tubing change. It is also desirable to keep the ENFit connector free from enteral feeding solution to avoid microbial growth in any residual solution that might remain between uses, particularly as microbial growth in the connector could lead to contamination of the feeding tube which could adversely affect the patient.

The ENFit connector on the enteral feeding tube is of particular concern due to the geometry of the design. The ENFit feeding tube connector includes a large female hub with female threads along the inner surface. In the center of the female hub is a tapered male fitting that forms the fluid path for the enteral feeding solution. Between the female hub and the tapered male fitting is a narrow annular gap in which enteral feeding solution can accumulate. The mating ENFit tubing administration set connector has a central female connector with male lugs on the outer surface. In use, the central female connector of the tubing administration set slides over the tapered male fitting of the feeding tube connector, creating the fluid path, while the male lugs of the tubing administration set connector engage with the female threads of the feeding tube connector, securely locking the connection to prevent accidental disconnection, and assuring a leak proof fluid path.

When the tubing administration set is attached to or removed from the feeding tube, enteral solution may leak from the end of the administration set into the narrow gap between the interior threaded wall of the female hub and the outer wall of the tapered male fitting. This gap, in combination with the floor of the female hub, is commonly referred to as "the moat". For illustrative purposes, reference is made to FIG. 1 which depicts a known ENFit feeding tube connector 1 having a narrow annular gap between threaded inner wall 2 of a female hub 3 and an outer wall 5 of a tapered male fitting 4. These surfaces, in combination with a floor 6 of the female hub 3, constitutes the moat or a moat region 7. More specifically, the dimensions of one standard ENFit connector 1 are approximately: 0.220" diameter male fitting; 0.400" inner diameter for female hub; diametric distance of 0.340" between threads; and 0.335" deep female hub. With this in mind, it should be clear that the moat of the standard ENFit connector is small and narrow, making it difficult to access and difficult to remove any solution present. Traditional absorbent swabs, such as cotton tipped or foam applicators, are too large to fit into the moat, and commonly available thin absorbent materials, such as absorptive tissues or gauze pads, lack the rigidity needed to reach the floor of the moat to dry and clean it effectively.

At present, there are basically three cleaning systems for ENFit feeding tube connectors. Two of these known cleaning systems are disclosed in U.S. Pat. Nos. 9,931,176, 10,675,121 and D842,565 to Davis, and U.S. Pat. No. 10,188,482 to Reinard, respectively. The commercial versions of both of these systems use bristle brushes to clean the moat. The third system of cleaning, as disclosed by the Global Enteral Device Supplier Association or GEDSA, involves the use of a toothbrush to clean the moat and connector. In general, these brush systems, although rather expensive, have been found to be fairly effective in removing the enteral solution after it has dried or caked, but the use of dry brushes on dried enteral solution creates particles of dried feeding solution which must subsequently be removed from the moat, such as by tapping the connector or flushing the same with fluid. When using water or a liquid cleaning solution, the fluid can wet the clothes of the patient, bed linens and/or surrounding area, so steps must be taken to contain the fluid. In any case, the brushes are not absorbent and therefore ineffective in removing any existing liquid or solution from the moat, thereby permitting liquid enteral feeding or cleaning fluids to remain in the moat. This moisture, particularly enteral feeding solutions which are high in nutrients, creates the opportunity for undesirable microbial growth.

Based on the above, there exists a need in the art for a device which can be employed to effectively dry a moat, defined as a narrow gap between an inner wall of a female hub and an outer wall of a male fitting of an ENFit or other medical connector, either before the drying and caking of a medical solution delivered through the connector or after cleaning the moat with a fluid.

SUMMARY OF THE INVENTION

The present invention is directed to a cleaning device for a moat region defined within a hub of a medical connector, such as an ENFit connector, wherein the cleaning device is specifically designed to effectively remove fluid and dry the moat, thereby minimizing the potential for bacterial growth in the hub. In accordance with the invention, the cleaning device takes the form of an absorbent block which can be inserted into the moat by extending about a central male fitting and into a gap between the male fitting and the inner wall of a female hub of the medical connector. The absorbency of the block enables the device to absorb any liquid in the moat and dry the moat between uses of the medical connector. In a preferred embodiment of the invention, the block takes the form of a tubular cylinder, but other configurations could be employed. At least in the case of an ENFit connector, the cleaning device can be employed alone, i.e., prior to drying and caking of any enteral feeding solution in the hub, or in combination with a brush-type or other cleaning tool used to first remove any existing dried and caked solution in the hub while leaving a residual cleaning fluid in the moat.

Additional objects, features and advantages of the present invention will become more readily apparent from the following detailed description of preferred embodiments when taken in conjunction with the drawings wherein like reference numerals refer to corresponding parts in the several views.

BRIEF DESCRIPTION OF THE DRAWINGS

FIGS. 5A and 5B show orientation and mechanical alteration of absorbent sheets of the cleaning device.

DETAILED DESCRIPTION OF PREFERRED EMBODIMENTS

Figure 1:
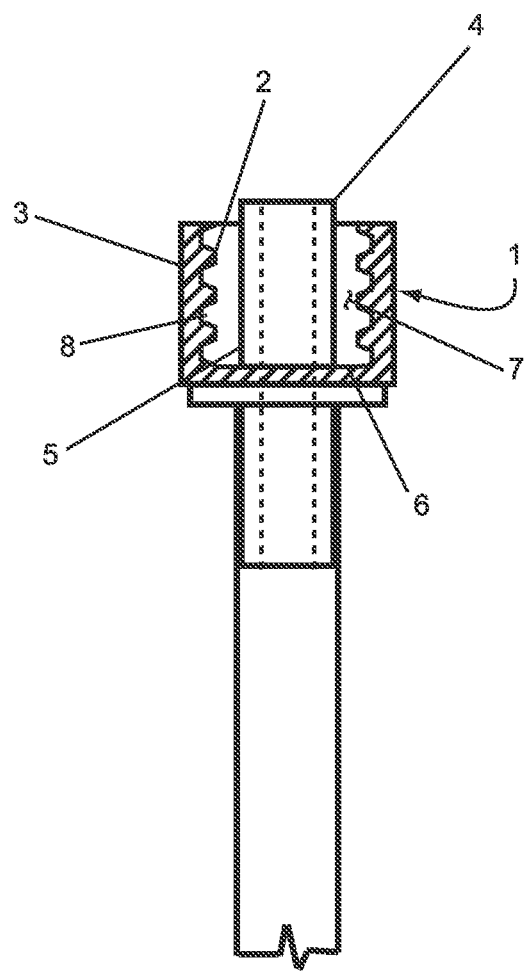
FIG. 1 is a cross sectional view of the standard ENFit feeding tube connector.
Figure 2:
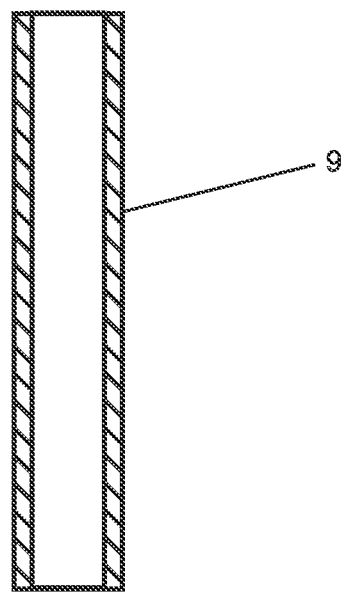
FIG. 2 is a cross sectional view of an absorbent cleaning device taking the form of a hollow cylinder or tube in accordance with a preferred embodiment of the invention.
Figure 3A:
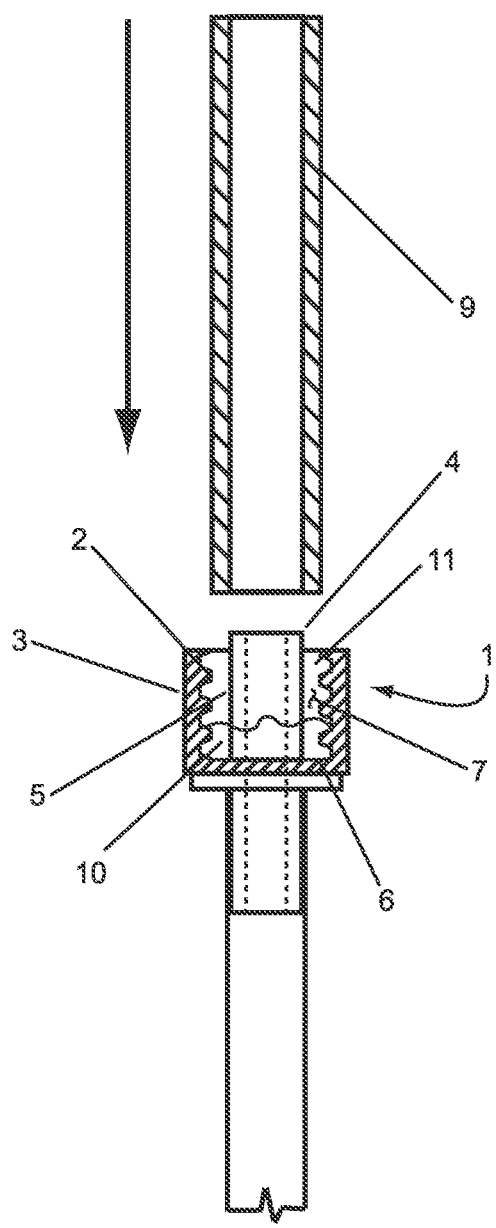
FIGS. 3 A to D show the use of the absorbent cleaning device with an ENFit feeding tube connector.
Figure 3B:
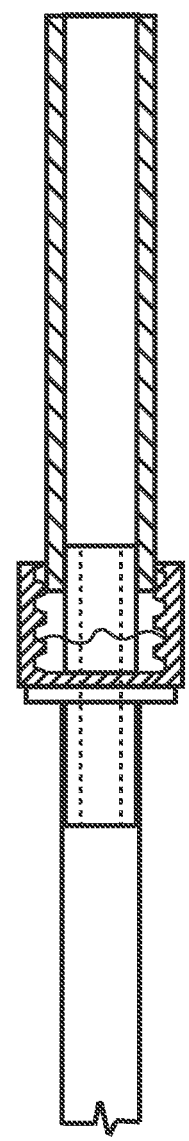
Figure 3C:
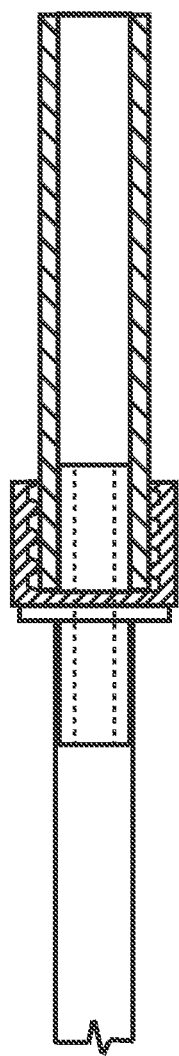
Figure 3D:
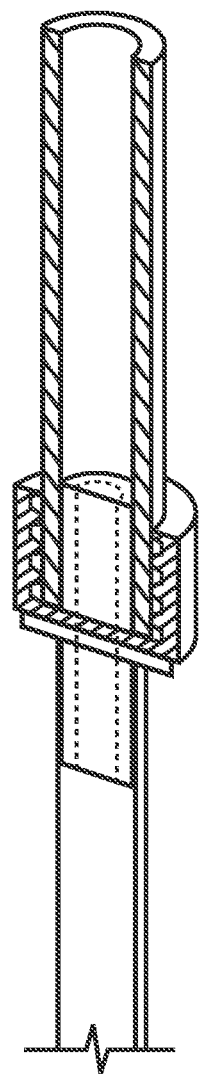

With initial reference to FIG. 2, a cleaning device 9 constructed in accordance with a preferred embodiment of the invention takes the shape of a hollow cylinder or tube formed from a liquid absorbent material. More specifically, absorbent cleaning device 9 is made of a highly absorbent material and is sized according to the geometry of the ENFit connector to be cleaned. More generally, cleaner device 9 is structurally configured in size and shape to conform to the requisite medical connector hub, with the exemplary embodiments shown being configured for particular use with a known ENFit connector, such as that shown in FIG. 1. As will be detailed more fully below, cleaner device 9 functions to remove fluid from the inner surfaces of the ENFit feeding tube connector, including the inner wall, the female thread paths, the floor of the female hub and the outer surface of the tapered male fitting in the center of the female hub, leaving this moat region and its defining surfaces clean and dry.

To accomplish the desired cleaning function, cleaning device 9 is long and narrow enough to fit within the geometry of the hub structure, and rigid enough to allow manipulation during the cleaning of all aspects of the hub. Further, cleaning device 9 is highly absorbent, with excellent wicking properties to remove all residual fluid from the hub, including from on and between the threads of the inside wall of the female hub. The cleaning device 9 may be formed from sheet material, die cut from a block of material, molded, or formed according to fabrication techniques particular to the material used. The absorbent materials may include natural materials such as woven or non-woven cellulose or cotton, or synthetic woven or non-woven fibers, or absorbent polymers such as poly vinyl acetate (PVA) or the like. Certainly, various absorbent materials having similar absorbent and other physical characteristics could be employed, such as for ease in fabrication, so long as the functionality in absorptive capability, stiffness and expansion upon wetting are maintained as detailed further below.

Figure 4:
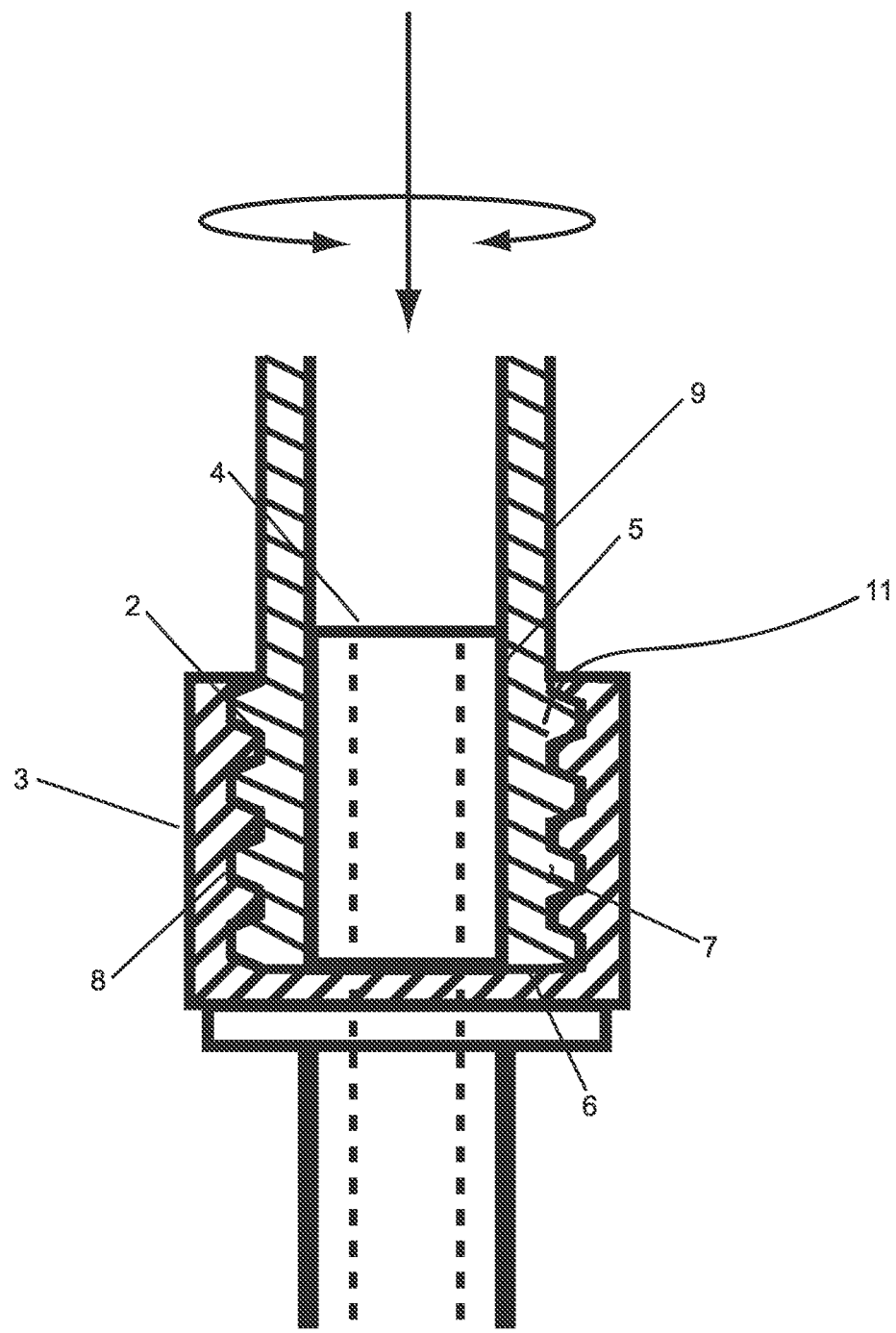
FIG. 4 shows the expansion of the absorbent cleaning device into internal female threads of the ENFit feeding tube connector during use in fluid removal.

FIGS. 3A-3D illustrate steps employed in using cleaning device 9 in absorbing fluids with the moat 7 of ENFit feeding tube connector 1. After disconnection of the ENFit tubing administration connector (not shown) from the ENFit feeding tube connector 1, cleaning device 9 is inserted into female hub 3. The cleaning device 9 fills the gap 7 between the inside wall 2 of the female hub 3 and the outer wall 5 of the tapered male fitting 4 as clearly shown in FIGS. 3B-3D, whereupon the highly absorbent material absorbs any fluid 10 that might remain in hub 3. Referring to FIG. 4, as the absorbent material of cleaning device 9 absorbs fluid 10 (labeled in FIG. 3), it will expand, filling the space 11 in moat 7 and wicking fluid from all portions of female hub 3, including between threads 8 along inner surface 2, floor 6 of hub 3, and walls 5 of tapered male fitting 4. Although cleaning device 9 is preferably configured to just be linearly and non-rotatably inserted to moat 7, if needed, such as if hub 3 contains a significant level of liquid which wets cleaning device 9 causing it to expand or cleaning device 9 is pre-wet prior to insertion, using a clockwise motion, the user can actually "screw" cleaning device 9 down to floor 6 of moat 7 to thoroughly clean threads 8. Regardless, the user can "unscrew", i.e., threadably withdraw, the expanded cleaning device 9 when the fluid absorption/drying operation, i.e., cleaning, is completed.

In one embodiment shown in FIG. 5A, an absorbent material 12, in the form of a sheet, is rolled into a hollow roll or cylinder (e.g., 1.750" in length) in forming cleaning device 9, with an inner diameter (e.g., slightly greater than 0.220") capable of passing over the tapered male fitting 4 in the center of the female hub 3 and an outer insertion diameter less than a diametric distance between the threads of hub 3. Again, upon the absorption of fluid and expansion, cleaning device 9 is configured to be compressed inside female hub 3. Multiple layers of absorbent material may be required, depending on the thickness of the material used, knowing that the roll of absorbent material must contact the inner walls 2, floor 6 and threads 8 of the female hub 3, as well as the outer wall 5 of the tapered male fitting 4, to provide thorough cleaning. The absorbent sheet 12 may also be rolled in a specific orientation according to the material used. For example, if an absorbent paper, e.g., cotton, is used, the absorbent sheet may be more easily rolled based on the grain direction 13 of the sheet. Additionally, the absorbent material may also be treated or mechanically altered to enhance rolling, such as by forming longitudinal ribs, either mechanically in the material, or by the addition of other materials, along the length of the rolled cylinder. For example, as illustrated in FIG. 5B, sheet 12 may be mechanically formed or treated, such as by creating mechanically formed polygon cross section shaped corrugations or flutes 14, to enhance both ease of rolling and the stiffness of the roll. In any case, with highly absorbent materials having rapid wicking capabilities employed in connection with the invention which may lose structural rigidity as they absorb fluid, the invention may employ a means to provide cleaning device 9 with structural integrity during use.

Figure 6A:
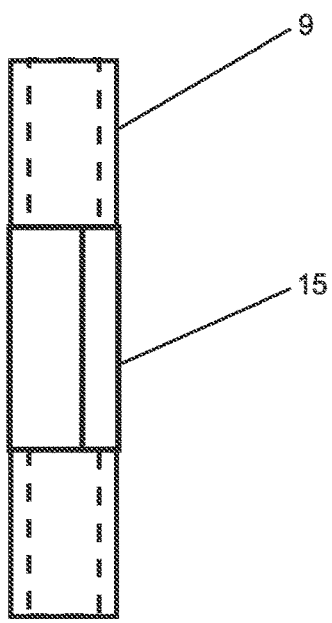
FIGS. 6A-C show different finger grip styles for use on the cleaning device.
Figure 6B:
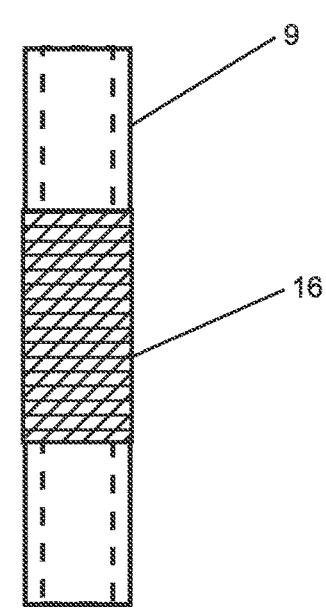
Figure 6C:
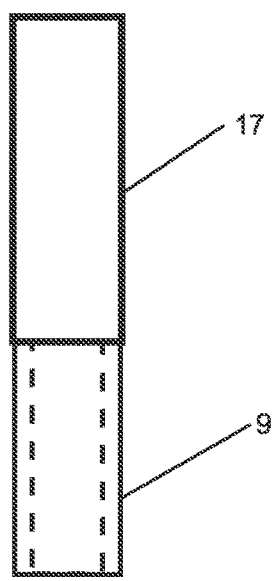

As illustrated in FIGS. 6 A-C, the rolled cleaning device 9 may be prevented from unrolling using components such as a tape or label 15 (FIG. 6A), a sleeve or band 16 (FIG. 6B) or an end cap 17 (FIG. 6C), all of which may be used as a finger rest to prevent the user's fingers from becoming wet as liquid is wicked into the material during use. These components may also be used in conjunction with each other to secure the absorbent material and prevent unrolling, while also providing a finger rest. As in FIGS. 6A and 6B, the finger rest may be located toward the middle of the cleaning device 9 if a two ended cleaner is desired, or at the end of the cleaning device 9 for a single ended cleaner, as in FIG. 6C. The finger rest may be secured to the absorbent material using various methods, such as with a pressure sensitive adhesive or a hot melt adhesive, by deforming the finger rest material by mechanical staking, or by melting the finger rest using heat or ultrasound to bond it to the absorbent material.

Figure 7:
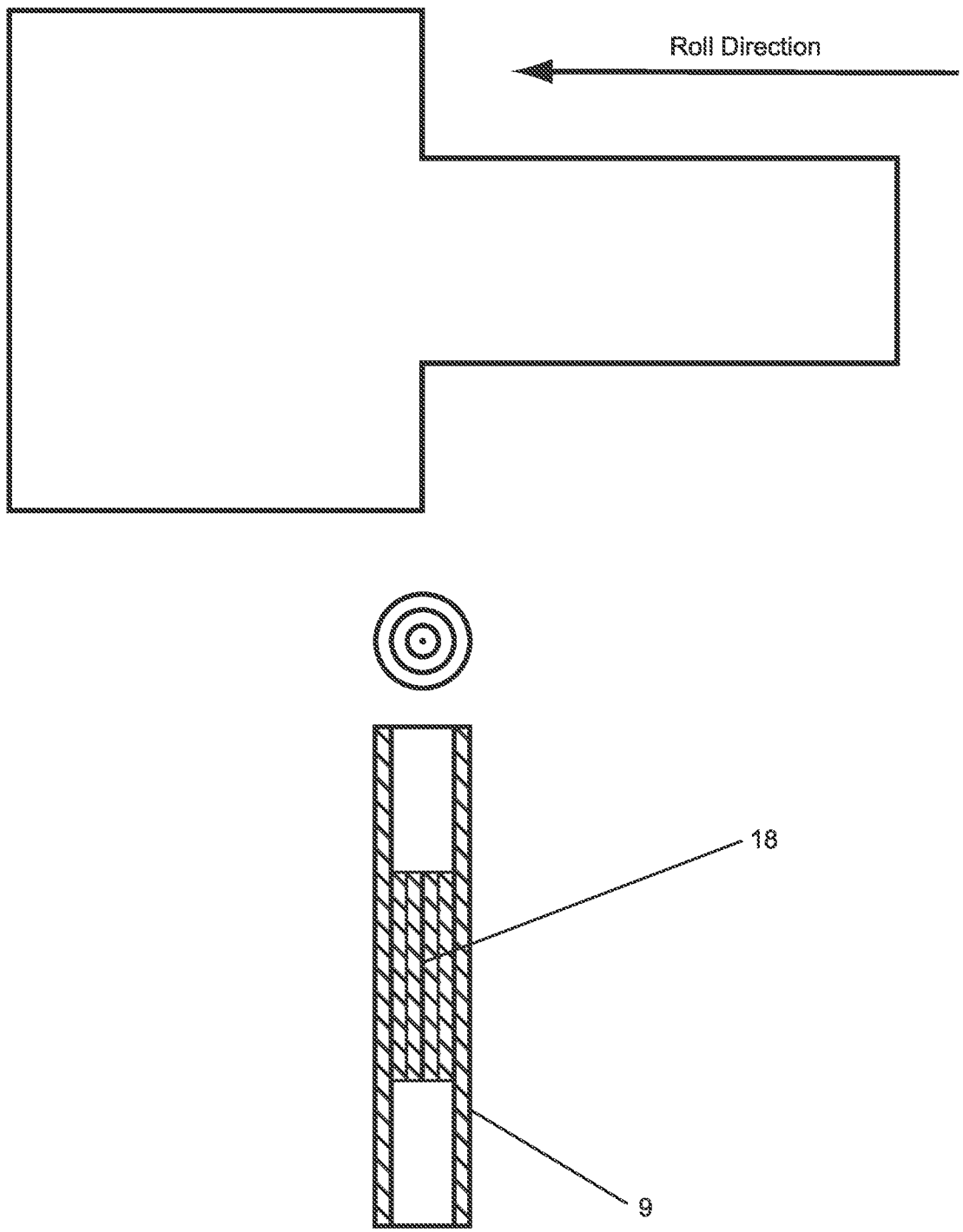
FIG. 7 shows how a core may be incorporated into the cleaning device.
Figure 8:
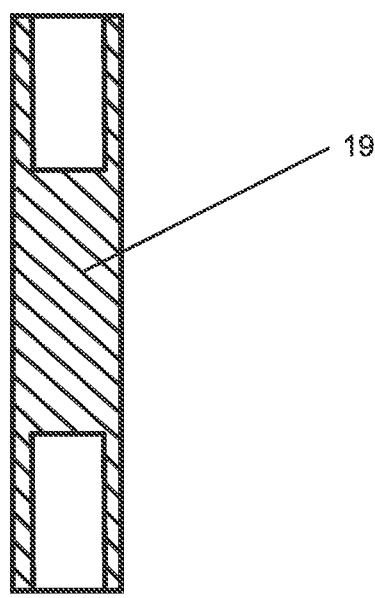
FIG. 8 is a cross sectional view of a cleaning device embodiment constructed in accordance with the invention employing an integral core.
Figure 9:
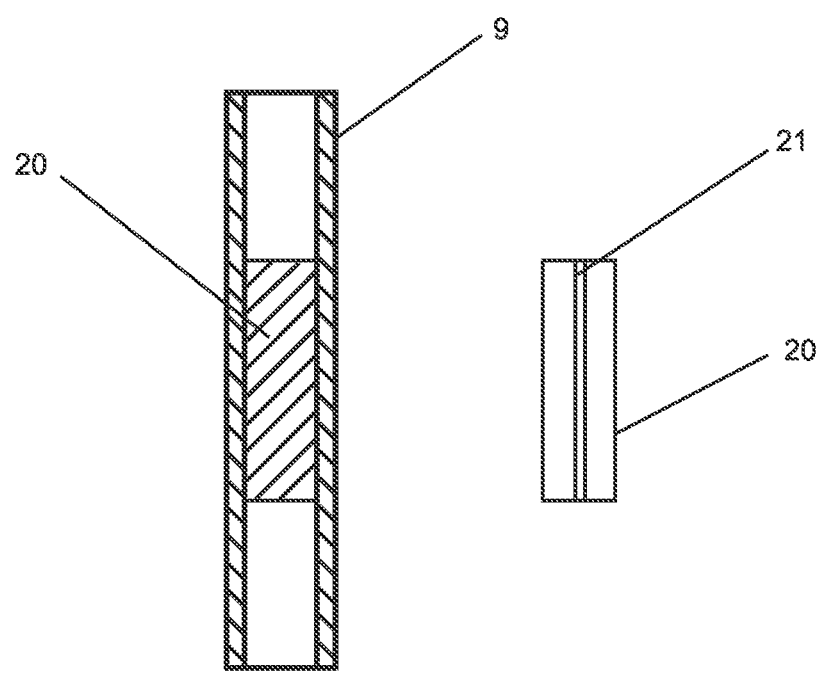
FIG. 9 is a cross sectional view of a cleaning device embodiment with a separate core.

In other embodiments designed for enhanced strength, a core element may be used, either alone or in combination with other strength enhancing arrangement described herein. Such a core element may be formed by using the absorbent material itself, or through the addition of another component or components. In one embodiment shown in FIG. 7, a core element 18 may be created by rolling enough additional absorbent material to fill at least a portion the hollow center of the absorbent cylinder, while still allowing clearance at the ends of the cylinder to accommodate the length of the tapered male fitting 4, or a secondary roll of either absorbent or non-absorbent material may be incorporated into the absorbent cylinder 9. In another embodiment shown in FIG. 8, the absorbent material is molded, formed or cut into a shape with varying thicknesses to create a unitary core region 19 providing increased structural integrity while still accommodating the length of the tapered male fitting 4. In a still further embodiment as shown in FIG. 9, a rigid or semi-rigid material is incorporated into the lumen (not labeled) of the cleaning device 9 to act as a core element 20. For example, a solid or hollow core element 20 of molded or extruded material could be incorporated into the outer body of cleaning device 9 during the rolling process to provide structural rigidity. Further, this core element may be used to facilitate rolling through the use of a longitudinal slot or groove 21 which accommodates the leading edge of the absorbent sheet.

Figure 10:
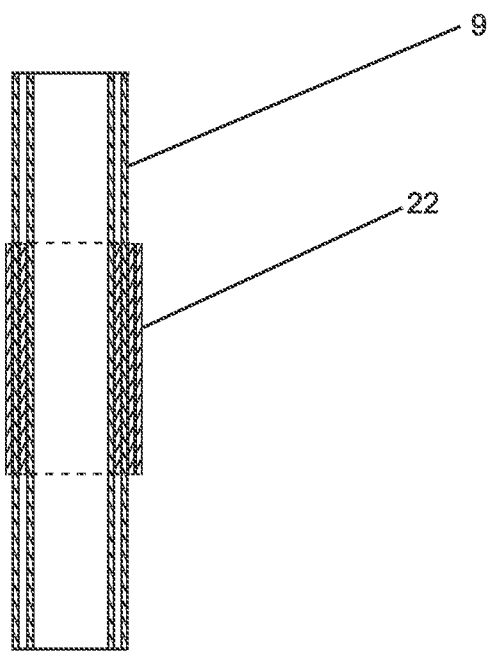
FIG. 10 is a cross sectional view of a cleaning device embodiment with an integrated finger grip.

In accordance with another aspect of the invention, with particular reference to FIG. 10, a tape or other semi-rigid material 22 may be incorporated into a roll of absorbent material to provide structural rigidity to the wall of the rolled cleaning device 9. For example, a pressure sensitive tape 22 could be applied to a sheet of the absorbent material and incorporated into cleaning device 9 as it is rolled. To prevent unrolling, an additional portion of tape 22 may extend beyond the edge of the absorbent material, while being used to secure a loose end of tape 22 to itself. In a manner analogous to that discussed above with particular reference to FIG. 6B, multiple layers of tape 22 could be used to provide different amounts of rigidity, while also acting as a finger grip.

At this point, it should be noted that, in connection with the arrangement of FIG. 6B, the incorporation of rigid or semi-rigid band 16 can also establish an additional way to improve the structural integrity around the exterior of the cleaning device. Band 16 could be in the form of an extruded or molded component, and may be a unitary component or formed from two or more components. That is, band 16 would provide enhanced structural rigidity and keep the absorbent cleaning device 9 from unrolling, while still acting as the finger grip to protect the user's fingers from becoming wet during use. Just as referenced above, band 16 could be secured to the absorbent material with adhesive, with heat or ultrasonic welding, heat staked, or by a mechanical means such as structures in a molded component to grip the absorbent material to prevent band 16 from sliding off the body of cleaning device 9. It should be further recognized that the referenced embodiment of FIG. 6C can establish another arrangement for providing structural integrity, while keeping the cleaning device from unrolling. That is, end cap 17 fastened to one end of the body of cleaning device 9 adds to the overall structural integrity. End cap 17 can have a closed or open end. In the case of a closed end cap 17, the body of cleaning device 9 is inserted into cap 17. An adhesive, such as hot melt glue, can be used to secure the body in end cap 17. Alternatively, end cap 17 could be molded with the body and incorporate structures to grip the absorbent material to prevent the body of cleaning device 9 from sliding out of end cap 17. Again, additional methods could be used to secure end cap 17 to the body of cleaning device 9, such as mechanical staking, welding or the like.

Figure 11:
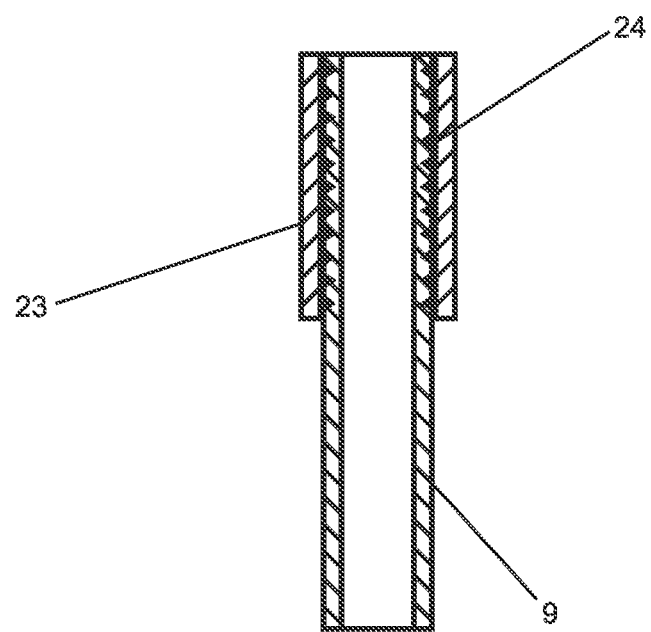
FIG. 11 is a cross sectional view of a cleaning device with and end cap or sleeve finger grip.
Figure 12:
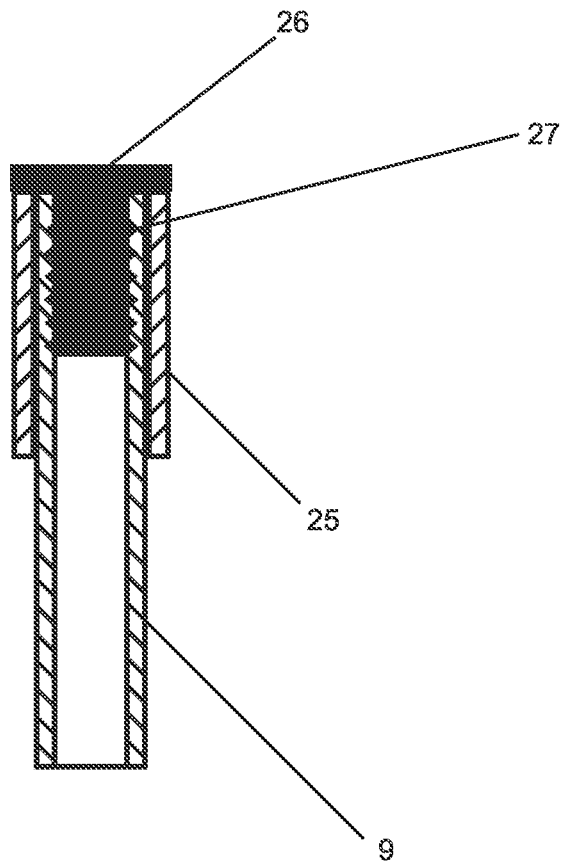
FIG. 12 is a cross sectional view of a cleaning device with and end cap or sleeve finger grip and an end plug.

In the case of an opened end cap as in FIG. 11, an open ended cap or sleeve 23 is provided at one end of the body for cleaning device 9. Open cap/sleeve 23 can be molded and incorporate structures 24 to grip the absorbent material to prevent the body of cleaning device 9 from sliding out of cap/sleeve 23, or the cap/sleeve 23 could be secured in various other ways, including being mechanically staked to the absorbent material, alone, or in conjunction with, heat or ultrasonic welding. An additional arrangement is shown in FIG. 12 for securing an open cap/sleeve 25 to the body of cleaning device 9 wherein an end plug 26 is used in conjunction with cap/sleeve 25. In this case, cap/sleeve 25 is placed over the body of cleaning device 9, and end plug 26 is inserted into the lumen of cleaning device 9, capturing the absorbent material between cap/sleeve 25 and end plug 26. End plug 26 can secured mechanically through the use of structures 27 to grip the absorbent material, via an interference press fit, or by being sealed to the cap/sleeve 25 using heat, ultrasound, or adhesive. The structures 27 could alternatively be located on cap/sleeve 25 (as in a manner similar to structures 24 of FIG. 11), or end plug 26 could be smooth or feature complementary elements to structures 27. The open ended cap/sleeve 25 and end plug 26 could also be combined into a singular component with similar features which could be placed over or around the end of cleaner device 9.

Figure 13:
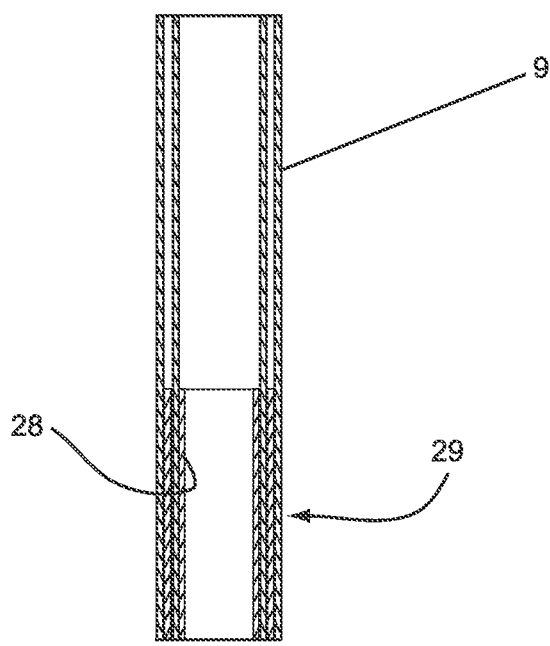
FIG. 13 is a cross sectional view of a cleaning device with an integrated stiffener at one end.
Figure 14:
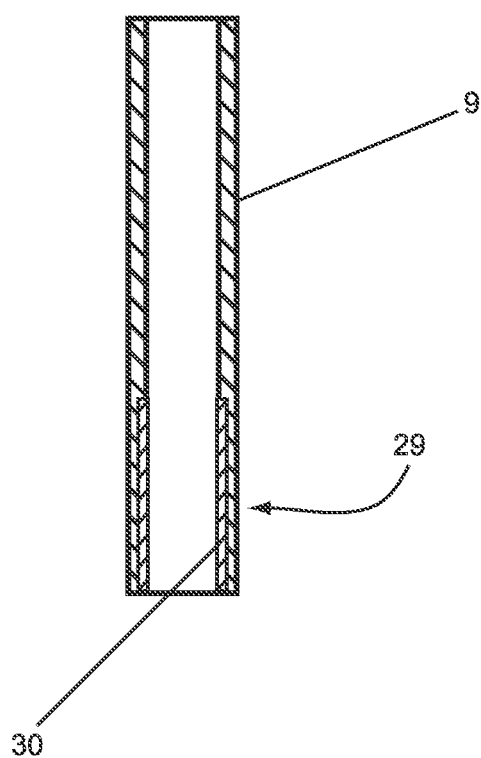
FIG. 14 is a cross sectional view of a cleaning device with a hollow core stiffener.

In some cases it may be desirable to wet the absorbent material of the cleaning device before it is inserted into the connector to provide a solvent to soften dried or partially dried enteral feeding solution during cleaning, or to apply a disinfecting solution. As mentioned above, the wetting may decrease the structural integrity of the body and make the cleaner device difficult to insert into the connector. To accommodate wet use, the cylinder can be fabricated from multiple materials, with at least one material providing absorbency and at least one other material providing structural rigidity. FIGS. 13 and 14 illustrate exemplary embodiments wherein a structural element is added to one end of cleaning device 9 to give it more rigidity at that end. In the embodiment of FIG. 13, a strip of semi-rigid material or tape 28 is incorporated within the hollow body of cleaner device 9 to reinforce a wettable end 29 or, as in the embodiment of FIG. 14, a hollow core 30 is positioned in the lumen of cleaning device 9 at wettable end 29. In either case, the stiffening material still allow cleaning device 9 to fit over the male fitting of a medical connector. The tape or semi-rigid material 28 of FIG. 13 or the hollow core 30 of FIG. 14 could have fenestrations or cutouts to allow absorbent material to be exposed to the surfaces of the female hub of the connector, while still providing increased rigidity.

Figures 15A, 15B:
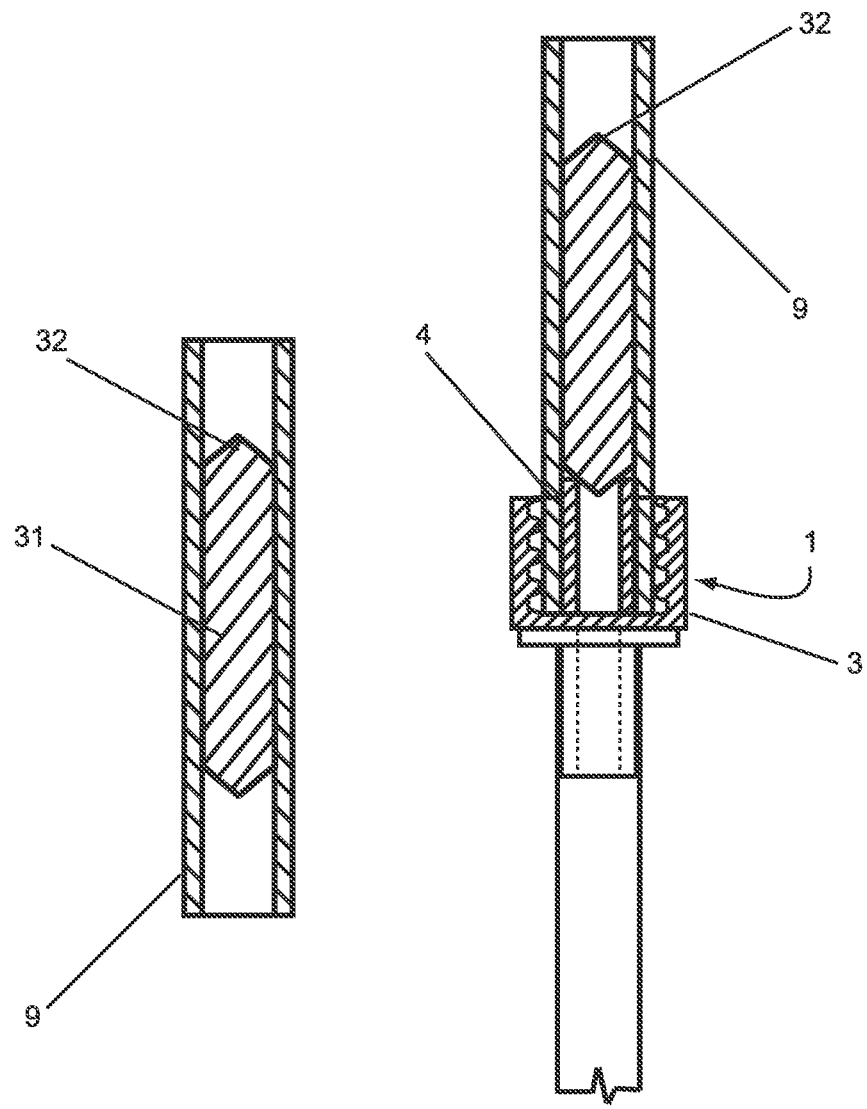
FIG. 15A-D show cross sectional views of cleaning devices with cores and fluid path plugs.
Figures 15C, 15D:
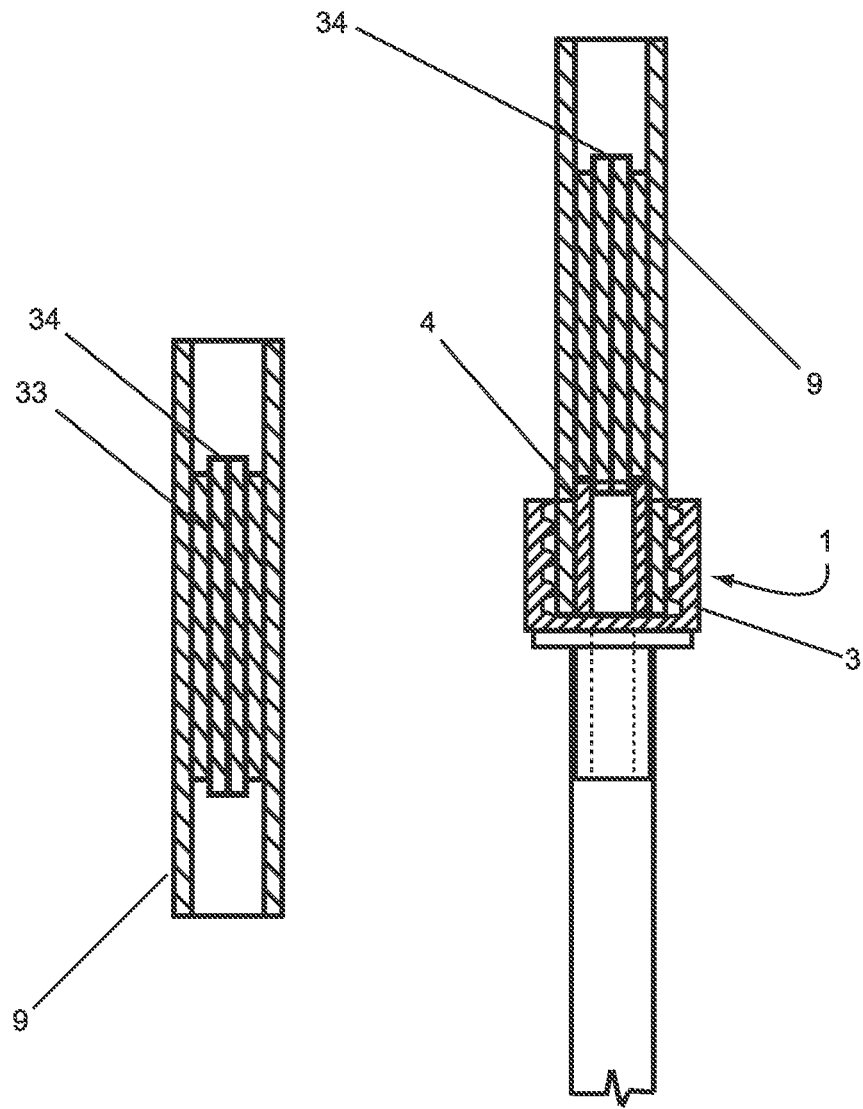

During a cleaning operation, it may be desirable to plug the end of the tapered male fitting of the medical connector to prevent liquid from entering the fluid path of the feeding tube and, subsequently, the patient, such as the patient's gastrointestinal tract. To address this concern, a plug may be created by incorporating a core into the cleaning device, with the core being shaped to have a geometry configured to occlude the lumen of the tapered male fitting when the cleaning device is applied to female hub. With initial reference to FIG. 15A, a core 31, having one or more core ends 32 and shown as a separate component from the body of cleaner device 9, is constructed from a conformable material such as an elastomeric polymer. Alternatively, as in the embodiment of FIG. 15C, a core 33, having one or more core ends 34, is created by filling a hollow interior of cleaning device 9 with absorbent material. The absorbent core 33 can be created in various ways, such as by rolling an appropriately sized and shaped piece of absorbent material into a structure such that core 33 and core ends 34 are formed during the rolling process, or alternatively core 33 could be formed using a separate piece of absorbent material incorporated as an integral part of the body of cleaning device 9. In either case, during use, pressure exerted by the user while cleaning the medical connector causes the core end 32 or 34 to press against, and conform to, the tapered male fitting 4, thus sealing the lumen as shown in FIG. 15B and FIG. 15D.

Figure 16:
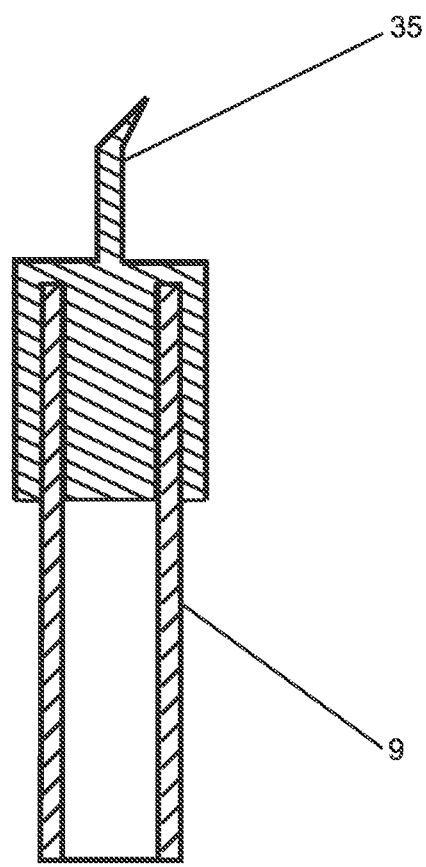
FIG. 16 is a cross section view of a cleaning device with a tool at one end.

There are times when a solution, such as an enteral solution, could dry and cake in the moat. As discussed above, brushes are currently used to remove these accumulations. However, in accordance with the invention, provisions are made to integrate a tool into one end of the cleaning device to facilitate removal of the dried material. FIG. 16 illustrates an exemplary embodiment wherein a supplemental molded or fabricated tool 35 is incorporated into a molded core or end cap, and secured to the upper end portion of cleaning device 9, such as through the use of adhesive, heat seal or ultrasound. Alternatively, the tool 36 could be formed integral with the body of the cleaning device 9 or by deforming an end cap or sleeve using a controlled heat or ultrasonic welding process either during or after attachment of the cap or sleeve to the upper end portion of cleaning device 9.

Although described with reference to preferred embodiments of the invention, it should be readily understood that various changes and/or modifications can be made to the invention without departing from the spirit thereof. Certainly, the skilled person will appreciate that the hub cleaning device described herein is not limited to use with an ENFit enteral feeding tube connector, but rather can be readily configured for use with a wide range of medical connectors including a moat region which is difficult to readily access for necessary cleaning purposes. In general, the invention is only intended to be limited by the scope of the following claims.

The invention claimed is:

1. A method of removing fluid from within a medical connector including a female hub having an inner threaded wall and a central male fitting annularly spaced from the inner threaded wall by a moat region with a cleaning device including a body constituted by an absorbent material, said method comprising:
    inserting the body of the cleaning device within the moat region, with a hollow interior portion of the body receiving the central male fitting; and
    removing fluid from within the medical connector by absorbing the fluid from within the moat region with the absorbent material of the cleaning device.

2. The method of claim 1, wherein inserting the body of the cleaning device within the moat region includes linearly and non-rotatably pushing the body to a floor of the female hub.

3. The method of claim 1, further comprising expanding the body of the cleaning device within the female hub upon the absorbent material getting wet by absorbing the fluid.

4. The method of claim 1, further comprising automatically sealing the central male fitting with a plug of the cleaning device upon inserting the body of the cleaning device within the moat region.

5. The method of claim 1, further comprising softening a dried enteral feeding solution with a solvent or applying a disinfecting solution within the female hub by wetting the absorbent material of the cleaning device before inserting the body into the medical connector.

6. The method of claim 1, further comprising cleaning dried and/or caked solution in the moat region, prior to insertion of the absorbent material of the body into the moat region, with a tool provided as part of the cleaning device.

7. The method of claim 1, wherein the absorbent material of the cleaning device expands upon becoming wet such that the body extends radially outward between threads of the inner threaded wall.

8. The method of claim 1, further comprising using natural materials consisting of woven or non-woven cellulose or cotton, synthetic woven or non-woven fibers, or one or more absorbent polymers of the body to absorb the fluid.

9. The method of claim 1, wherein the body has a form of a tube or hollow cylinder for absorbing the fluid.

10. The method of claim 7, wherein the body of the cleaning device is linearly and non-rotatably inserted to a floor of the female hub.

11. The method of claim 10, wherein the body of the cleaning device is threadably withdrawn from within the female hub.

\* \* \* \* \*